(12) United States Patent
Giordano et al.

(10) Patent No.: US 6,448,007 B1
(45) Date of Patent: Sep. 10, 2002

(54) FUNCTIONAL GENOMIC SCREEN FOR POST-TRANSCRIPTIONAL 5' AND 3' REGULATORY ELEMENTS

(75) Inventors: Tony Giordano, Phoenixville; Gordon D. Powers, Malvern; Paul S. Eder, Oreland; Bonnie-Ann Burnett, Malvern; Gretchen L. Temeles, Ardmore, all of PA (US)

(73) Assignee: Message Pharmaceuticals, Malvern, PA (US)

( * ) Notice: Subject to any disclaimer, the term of this patent is extended or adjusted under 35 U.S.C. 154(b) by 0 days.

(21) Appl. No.: 09/603,522

(22) Filed: Jun. 23, 2000

Related U.S. Application Data (60) Provisional application No. 60/142,217, filed on Jul. 2, 1999.

(51) Int. Cl.$^7$ .................. C12Q 1/68; C12P 19/34; C12N 1/12; C12N 1/20; C12N 15/00
(52) U.S. Cl. .................. 435/6; 435/91.1; 435/252.1; 435/320.1; 536/23.1
(58) Field of Search .................. 435/6, 91.1, 252.1, 435/320.1; 536/23.1

(56) References Cited

U.S. PATENT DOCUMENTS

| | | | |
|---|---|---|---|
| 5,968,738 A | * | 10/1999 | Anderson et al. .............. 435/6 |
| 6,083,727 A | | 7/2000 | Guegler et al. ............ 435/91.5 |

FOREIGN PATENT DOCUMENTS

| | | |
|---|---|---|
| WO | WO 94/23041 | 10/1994 |
| WO | WO 98/42854 | 10/1998 |
| WO | WO 98/55502 | 12/1998 |

OTHER PUBLICATIONS

Gao, F–B. et al., "Selection of a subset of mRNAs from combinatorial 3' untranslated region libraries using neuronal RNA–binding protein He1–N1", PNAS USA vol. 91, pp. 11207–11211, 1994.*
Carrier T.A. et al., "Library of Synthetic 5' Secondary Structures To Manipulate mRNA Stability in *Escherichia coli*", Biotechnol. Prog. vol. 15, pp. 58–64, 1999.*
Donis–Keller et al., "Site Specific Enzymatic Cleavage of RNA," Nucl. Acids Res. 7:179–192 (1979).
Grignani et al., "High Efficiency Gene Transfer and Selection of Human Hematopoietic Progenitor Cells with a Hybrid EBV/Retroviral Vector Expressing the Green Fluorescence Protein," Cancer Res. 58:14–19 (1998).
Kozak et al., "An Analysis of 5'–Noncoding Sequences from 699 Vertebrate Messenger RNAs," Nucl. Acids Res. 15:8125–8148 (1987).
Spicher et al., "Highly Conserved RNA Sequences That Are Sensors of Environmental Stress," Molecular and Cellular Biology, 18:7371–7382 (1998).
Suzuki et al., "Construction And Characterization Of A Full Length–enriched And A 5'–end–enriched cDNA Library," *Gene* 200:149–156 (1997).

* cited by examiner

*Primary Examiner*—Kenneth R. Horlick
*Assistant Examiner*—Teresa Strzelecka
(74) *Attorney, Agent, or Firm*—Clark & Elbing, LLP (57) ABSTRACT

The invention features cDNA libraries consisting essentially of cDNA sequences that correspond to different mRNA untranslated region (UTR) sequences separate from adjacent mRNA coding sequences. The invention also features methods for generating these libraries and for identifying a regulatory UTR sequence.

33 Claims, 4 Drawing Sheets

LANES: 1 2 – 3 4 5 – 6 7 – 8 9 –10

1 Kb ladder
100 bp ladder
total RNA stock
poly (A) + RNA
poly (A) + RNA; no enzyme
poly (A) + RNA; NNCATNN 30' or 60'
poly (A) + RNA; GCCATGG 30' or 90'
100 bp ladder

FUNCTIONAL GENOMIC SCREEN FOR POST-TRANSCRIPTIONAL 5' AND 3' REGULATORY ELEMENTS

Cross Reference to Related Applications

This application claims priority from U.S. Provisional Application Ser. No. 60/142,217, filed Jul. 2, 1999.

FIELD OF THE INVENTION

This invention relates to the field of nucleic acid regulatory elements that affect mRNA translation, export, and stability. More specifically, the invention relates to the screening of 5' and 3' untranslated RNA sequences, the identification of RNA regulatory elements within these sequences, and the identification of compounds that modulate the function of these RNA regulatory sequences.

BACKGROUND

While transcriptional controls regulate gene expression by influencing the rate of mRNA production, post-transcriptional mechanisms can also regulate gene expression by modulating the amount of protein produced from an mRNA molecule. For example, gene expression can be regulated by altering mRNA translation efficiency (Izquierdo and Cueza, Mol. Cell Biol. 17: 5255–5268, 1997; Yang et al., J. Biol. Chem. 272: 15466–73, 1997), or by altering mRNA stability (Ross, Microbiol. Rev. 59: 423–50, 1995). Post-transcriptional control mechanisms appear to play an especially important role in the gene expression response to environmental factors, such 1s response to heat shock (Sierra et al., Mol. Biol. Rep. 19: 211–20, 1994), iron availability (Hentze et al., Proc. Natl. Acad. Sci. USA 93: 8175–82, 1996), oxygen availability (Levy et al., J. Biol. Chem. 271: 2746–53, 1996; McGary et al., J. Biol. Chem. 272: 8628–34, 1997), and growth factors (Amara et al., Nucleic Acids Res. 21: 4803–09, 1993).

Post-transcriptional regulatory elements may be present in the 5' and 3' mRNA untranslated regions (UTRs). At the 5' UTR, mRNA binding to ribosomes is generally the rate-limiting step in translation initiation (Mathew et al., In: Translational Control, pages 1–30, Eds: Hershey et al., Cold Spring Harbor Laboratory Press, Cold Spring Harbor, N.Y., 1996). At the 3' UTR, regulatory elements may modulate mRNA translation and degradation, as well as mRNA transport and subcellular localization (Jackson, Cell 74: 9–14, 1993). However, the nature of most UTR post-transcriptional elements remains poorly understood. A method for efficiently characterizing these mRNA regulatory sequences would advance the discovery of compounds that modulate expression of therapeutically important proteins via regulatory mRNA sites.

SUMMARY OF THE INVENTION

We have discovered a method for constructing libraries that are specifically biased for RNA regulatory sites. In the first aspect, the invention features a cDNA library consisting essentially of at least 100 different cDNA sequences that correspond to different mRNA untranslated region (UTR) sequences isolated and separate from adjacent mRNA coding sequences. Preferably, the cDNA sequences are cloned into a vector system that can express the sequences, and such a vector is also a feature of this invention. This vector includes the following: a) a nucleotide sequence encoding an mRNA UTR sequence in operative linkage to a promoter, wherein the nucleotide sequence is derived from the cDNA library of the first aspect; b) a first reporter gene positioned for transcription upstream or downstream of the UTR-encoding nucleotide sequence; and c) a second, different reporter gene in operative linkage to a promoter but unassociated with the UTR-encoding nucleotide sequence. Preferably, the reporter genes encode a fluorescent protein or cell surface marker protein.

A second and related aspect of the invention features a cDNA library, wherein the library is constructed by steps that include the following: a) purifying poly(A)+ RNA from total RNA; b) performing controlled, non-random enzymatic digestion of AUG sequences in the poly(A)+ RNA; c) purifying the digested RNA to obtain the fragments containing the 5' end sequences; and d) synthesizing cDNA from the purified RNA obtained in step (c); wherein the library consists essentially of cDNA sequences corresponding to mRNA 5' untranslated region (UTR) sequences, isolated and separate from adjacent mRNA coding sequences. Preferably, the enzymatic digestion is carried out using RNase H.

In a third aspect, the invention features a cDNA library constructed by steps that include the following: a) purifying poly(A)+ RNA from total RNA; b) synthesizing nucleic acid heteroduplexes from the poly(A)+ RNA using degenerate primers that hybridize preferentially to the region surrounding and including the initiation codon, where the heteroduplexes comprises the 5' end sequences of the RNA; c) purifying the heteroduplexes obtained in step (b) to obtain the fragments containing the 5' end sequences; and d) synthesizing cDNA from the purified heteroduplexes obtained in step (c); wherein the library consists essentially of cDNA sequences corresponding to mRNA 5' untranslated (UTR) sequences, isolated and separate from adjacent mRNA coding sequences.

In one embodiment of any of the above three aspects of the invention, the cDNA library consists essentially of cDNA sequences corresponding to mRNA untranslated region sequences, isolated in intact form.

In preferred embodiments of the second or third aspects of the invention, the 5' sequence purification is carried out using a cap binding protein, for example, an eIF4E fusion protein or an antibody to the 5' cap, and the DNA sequences are cloned into a vector system that can express the sequences. This vector includes the following: a) a nucleotide sequence encoding an mRNA UTR sequence in operative linkage to a promoter, wherein the nucleotide sequence is derived from the cDNA library of the second or third aspect; b) a first reporter gene positioned for transcription upstream or downstream of the UTR-encoding nucleotide sequence; and c) a second, different reporter gene in operative linkage to a promoter but unassociated with the UTR-encoding nucleotide sequence. Preferably, the reporter genes encode a fluorescent protein or cell surface marker protein.

A related fourth aspect of the invention is a cDNA library, wherein the library is constructed by steps that include the following: a) purifying poly(A)+ RNA from total RNA; b) performing random digestion on the poly(A )+ RNA; c) purifying the digested RNA to obtain poly(A) containing fragments; and d) synthesizing cDNA from the purified RNA obtained in step (c); wherein the library consists essentially of cDNA sequences corresponding to 3' UTR sequences, isolated and separate from adjacent mRNA coding sequences.

A cDNA library is also featured in the fifth aspect of the invention. This cDNA library is constructed by steps that include the following: a) purifying poly(A)+ RNA from total RNA; b) loading the poly(A)+ RNA with ribosomes; and c) performing reverse transcription on the loaded poly(A)+ RNA using an oligo(dT) primer and polymerase; wherein the library consists essentially of cDNA sequences corresponding to 3' UTR sequences, isolated and separate from adjacent mRNA coding sequences. Preferably, the cDNA sequences of the libraries of the fourth or fifth aspects are cloned into vector systems that can express the sequences, and such vectors are also a feature of this invention. These vectors include the following: a) a nucleotide sequence encoding an mRNA UTR sequence in operative linkage to a promoter, wherein the nucleotide sequence is derived from the cDNA library of the fourth or fifth aspect; b) a first reporter gene positioned for transcription upstream or downstream of the UTR-encoding nucleotide sequence; and c) a second, different reporter gene in operative linkage to a promoter but unassociated with the UTR-encoding nucleotide sequence. Preferably, the reporter genes encode a fluorescent protein or cell surface marker protein.

In one embodiment of the fourth or fifth aspect the invention, the cDNA library consists essentially of cDNA sequences corresponding to 3' untranslated region sequences, isolated in intact form.

A sixth aspect of the invention provides a method of identifying a regulatory UTR sequence that includes the following steps: a) transfecting a plurality of host cells with a plurality of vectors of the present invention, wherein the host cells are transfected with different UTR sequences; b) sorting cells on the basis of the ratio between expression of the first reporter gene and the second reporter gene; c) identifying the cells of step a) that have skewed expression ratios as compared to the population of cells of step (a) as a whole, or as compared to cells transfected with a vector that encodes the first and second reporter gene, but lacks the corresponding UTR sequence; and d) sequencing the UTR expressed in the identified cells. Preferably, the gene expression is detected by emission of fluorescence and the cells are sorted by a fluorescence activated cell sorter.

The seventh and final aspect of the invention features a cell transfected with any of the vectors of the present invention.

By "different mRNA untranslated region (UTR) sequences" or "different UTR sequences" is meant sequences that differ from each other in that they are derived from different mRNA species. As used herein, mRNA UTR sequences that are products of alternated splicing are considered to be different mRNA UTR sequences.

By "controlled, non-random enzymatic digestion of AUG sequences" is meant preferentially digesting mRNA at the site of AUG sequences, for example, using RNase H and a mixture of degenerate AUG-complementary oligonucleotide 7-mers, under conditions that require hybridization of more than 5 consecutive base pairs for RNase substrate recognition. To preferentially digest the initiation-AUG sequences in an mRNA population, the 7-mers in the AUG-complementary olgonucleotide mixture used have frequencies of A, C, G, and T at each position that are complementary to the frequencies of A, C, G, and U occurring in all known vertebrate mRNA sequences between the −3 and +4 position (where +1 is the first nucleotide of the coding sequence) (see, e.g., Table 1).

By "UTR sequences isolated and separate from adjacent mRNA coding sequences" is meant the following: 1) 5' UTR sequences that begin at the 5' end of a transcribed mRNA and extend up to, but do not include, the translation AUG initiation site; and 2) 3' UTR sequences that begin at the mRNA nucleic acid in the position 3' adjacent to the translation termination site and extent the poly(A) tail of the transcribed mRNA. Preferably, the UTR sequences are isolated n intact form.

By "random digestion" of poly(A)+ RNA is meant RNase digestion using, for example, RNase H and random primers to digest the RNA into smaller fragments at random sites.

By "loading poly(A)+ RNA with ribosomes" is meant contacting the RNA population with ribosomes, for example, in a rabbit reticulocyte lysate, to allow for loading of the ribosomes onto the RNA. To maximize ribosome loading, a chemical that prevents ribosome runoff, for example, cycloheximide, can be included.

By a "plurality" is meant more than one.

By "skewed expression ratios" is meant a change in the ratio of expression of a first reporter gene that is associated with a specific UTR to expression of a non-UTR associated second reporter gene, as compared to the ratio of expression of the first reporter gene that is not associated with the same UTR compared to expression of the non-UTR associated second reporter gene.

The screening assay and the 5' and 3' mRNA untranslated region (UTR) biased cDNA libraries of the present invention have a number of advantages. The biased UTR libraries provide a collection of UTR sequences that are isolated and separated from any adjacent coding sequences. Thus, screening these libraries allows opportunity to screen essentially complete UTR sequences without interference from coding sequences. In addition, the quantity of sequences screened and the specificity of output can be modulated by controlling conditions that regulate the number of different plasmids that enter each cell. In most circumstances, the ideal number of plasmids per cell would be limited to one, thereby reducing signal dilution and the occurrence of false negative results.

Other features and advantages of the invention will be apparent from the detailed description thereof and from the claims.

DETAILED DESCRIPTION

The practice of the present invention employs conventional techniques in biochemistry, molecular biology, microbiology, and related fields that are known to those skilled in the art. These techniques are fully explained in the literature (see, e.g., Maniatis et al., Molecular Cloning: A Laboratory Manual, Cold Spring Harbor Laboratory Press (1982); Sambrook et al., Molecular Cloning: A Laboratory Manual, Second Edition, Cold Spring Harbor Laboratory Press (1989); and Ausubel et al., Current Protocols in Molecular Biology, John Wiley & Sons (1987–1996 ed.)

Construction of UTR Libraries

Poly(A)+ RNA is isolated from total cellular RNA, according to standard protocol (Aviv and Leder, Proc. Natl. Acad. Sci. USA 69: 1408–12, 1972).

To construct 5' UTR biased libraries, poly(A)+ RNA is subjected to controlled, non-random enzymatic digestion followed by size selection. The enzymatic digestion of the poly(A)+ RNA is carried out, for example, using E. coli RNase H in the presence of a 7-mer oligodeoxynucleotide mixture, wherein the sequences of the oligodeoxynucleotides have A, C, G, and T at frequencies of occurrence that are complementary to the frequencies of occurrence of A, C, G, and U in all known vertebrate mRNA sequences between the −3 and +4 positions of the mRNA (where position 1 of the oligodeoxynucleotide is complementary to position +4 on the mRNA and position 7 is complementary to position −3 on the mRNA; see Table 1).

TABLE 1

Designing Degenerate Oligonucleotides for the Isolation of 5' UTRs

|  |  | +4 | +3 | +2 | +1 | −1 | −2 | −3 |
| --- | --- | --- | --- | --- | --- | --- | --- | --- |
|  | 7-mer oligo-deoxy-nucleotide position | 1 | 2 | 3 | 4 | 5 | 6 | 7 |
| 7-mer oligo-deoxynucleotide frequency (%) | A | 15 | 0 | 100 | 0 | 9 | 11 | 1 |
|  | C | 46 | 100 | 0 | 0 | 21 | 13 | 36 |
|  | G | 16 | 0 | 0 | 0 | 55 | 49 | 2 |
|  | T | 23 | 0 | 0 | 100 | 15 | 27 | 61 |

Given that E. coli RNase H requires hybridization of four consecutive base pairs in order to recognize a DNA/RNA duplex region as a substrate (Donis-Keller, Nucleic Acids Res. 7: 179–192, 1979), the controlled RNase H digestion using the above-described oligodeoxynucleotides will primarily hydrolyze the initiation codon, but because of the degeneracy of the oligodeoxynucleotide mixture, and the minimum consecutive number of base pairs required under physiological conditions, RNase H can also hydrolyze the RNA at many other locations, including regions in the 5' UTR. To further restrict the digestion to the initiation codon, conditions can be modified such that RNase H recognition requires hybridization of more than five base pairs (see Example 1). The AUG sequence is rare within the 5' UTR sequences (Kozak, Nucleic Acids Res. 15: 8125–48, 1987). Therefore, this RNase H digestion preferentially result in intact, full-length 5' UTR sequences that are separated from the adjoining coding sequences.

To enrich the population of 5' UTR-containing fragments within the mRNA sample, fragments of up to 1000 nucleotides are selected using denaturing agarose gels. The 5' UTRs of most vertebrate mRNAs fall within the size range of 20–100 nucleotides (Kozak, supra). Subsequent to size selection, the mRNA sample is subjected to affinity purification using a recombinant eIF4E fusion protein that interacts with the mRNA 5' cap structure (Sonenberg and Gingras, Curr. Opin. Cell Biol. 10: 268–75, 1998).

An alternative strategy for isolating 5' UTRs from purified poly(A)+ RNA is to reverse transcribe the poly(A)+ RNA using a degenerate (i.e., mixed-sequence) primer that hybridizes preferentially to the region surrounding and including the initiation codon (the 3' border of the 5' UTR).

The consensus sequence surrounding the initiation codon of vertebrate mRNAs is GCC (G/A)CC AUG G (SEQ ID NO: 1), where the underlined sequence is the initiation codon, and the nucleotides in parentheses are found with nearly equal frequency at that position.

A degenerate primer complementary to this consensus sequence can be designed that takes into account all the variations in frequency of the nucleotides at each position, so that the primer mixture has a high probability of hybridizing specifically to the initiation codon region. Table 2, below, shows that primers can be designed, based on the known sequences of hundreds of vertebrate mRNAs.

TABLE 2

Designing Degenerate Primers for the Isolation of 5' UTRS

| mRNA 3' | +4 | +3 | +2 | +1 | −1 | −2 | −3 | −4 | −5 | −6 | 5' |
| --- | --- | --- | --- | --- | --- | --- | --- | --- | --- | --- | --- |
| Primer 5' | 1 | 2 | 3 | 4 | 5 | 6 | 7 | 8 | 9 | 10 | 3' |
| % A | 10 | 0 | 100 | 0 | 10 | 10 | 5 | 10 | 20 | 20 |  |
| % C | 50 | 100 | 0 | 0 | 20 | 15 | 30 | 15 | 20 | 45 |  |
| % G | 20 | 0 | 0 | 0 | 55 | 50 | 5 | 50 | 40 | 20 |  |
| % T | 20 | 0 | 0 | 100 | 15 | 25 | 60 | 25 | 20 | 15 |  |

Data based on Kozak, Nucleic Acids Res. 15, 8125–8148, 1987 and Kozak, Gene 234: 187–208, 1999.

Referring to Table 2, the mixed-sequence primer reading 5' to 3' is complementary to the mRNA sequence surrounding the initiation codon. The numbering across the top from +4 through −6 corresponds to the numbering for the mRNA sequence, where position +1 is the first nucleotide of the initiation codon, and all the negative numbers refer to nucleotides in the 5' UTR. The percentages refer to the frequency of occurrence of a given nucleotide at a given position. Therefore, he primer would be synthesized such that, for example, at position 5, A occurs 10% o the time, C occurs 20% of the time, G occurs 55% of the time, and T occurs 15% of the time. Note that positions 2, 3, and 4 are invariant as they are complementary to the initiation codon, AUG. It is expected that a degenerate primer of the above composition would hybridize preferentially to the region of the mRNA surrounding and including the initiation codon.

Following RT-PCR to generate a minus strand cDNA hybridized to mRNA, the heteroduplex can be isolated by affinity purification of the complex. The mRNA/cDNA hybrids are incubated with either a monoclonal antibody to the 5' cap or a cap-binding protein, for example, an eIF4E protein attached to a solid matrix, washed and eluted to enrich for RNAs containing the full 5' UTR. Following elution of the complex, the RNA is digested with RNase H and terminal transferase is used to label the 3' end of the cDNA with poly d(T). Poly d(A) is then be used to prime the second strand synthesis of the cDNA. The 5' UTR enriched library is then cloned 5' to the reporter gene.

To construct the 3' UTR biased libraries, poly(A)+ RNA is digested, for example, using random primers and E. coli RNase H, followed by selection of poly(A)-containing fragments using oligo(dT)-linked resin. The isolated poly(A)-containing fragments are incubated with reverse transcriptase using oligo(dT) primers. Alternatively, to retrieve mRNA that is exclusively 3' UTR, isolated RNA is allowed to associate with ribosomes, for example, in lysates from rabbit reticulocytes. Under conditions in which ribosome run-off is inhibited by cycloheximide, reverse transcription is performed in the presence of oligo(dT) and a low efficiency polymerase (see Example 2).

The purified 5' and 3' UTR RNA fragments are subjected to 5' RACE (Rapid Amplification of cDNA Ends) to obtain double-stranded cDNA (Frohman, In: PCR Protocols: A Guide to Methods and Applications, pages 28–38, Eds: Innis et al., Academic Press, London). The 5' or 3' UTR cDNAs are then ligated into an expression vector of choice, for example, a retroviral vector. The 5' and 3' UTR sequences are positioned upstream or downstream, respectively, of a reporter gene's coding sequence.

Screening Assay

The expression vectors used for transfection of host cells each encode one UTR, in operative linkage to a promoter, linked to its UTR-associated first reporter gene. The vector also includes a second, different reporter gene that is operably linked to a promoter, but is not associated with the UTR. Expression of this UTR-independent second reporter gene is not regulated by any UTR effect. Thus, expression of this second reporter gene controls for differences in expression that result from variations in plasmid number or transcriptional efficiency. In addition, conditions can be varied to reduce the number of different vectors, and, thus, the number of UTRs, that are introduced into each cell. To carry out host cell transfection, conditions are adopted to limit transfection, preferably, to less than 5 plasmids per cell, most preferably, to one plasmid per cell. Usually, it is preferable to identify conditions that allow nearly clonal delivery of the vectors to the cells. For retroviral transduction methods, cells are infected at a multiplicity of infection (MOI) such that each cell is infected with approximately one virus. The MOI can be determined empirically for each cell line and construct. Alternatively, plasmids can be delivered to cells via protoplast fusion (Tan and Frankel, Proc. Natl. Acad. Sci. 95:4247–52, 1998). For this method, *E. coli* are transformed with plasmid libraries, the bacteria cell walls are remove and the resulting protoplasts are fused to mammalian cells with polyethylene glycol. By adjusting the ratio of protoplasts to mammalian cells, plasmid delivery is reported to nearly clonal, with individual cells containing 1000 copies of a single plasmid.

The choice of cell type to be used will depend on several factors, for example, the biological system of interest and the ease of foreign DNA transfection. Thus, if the biological system of interest is breast cancer-related genes, a breast cancer cell line may be used. In addition, given that retroviral transduction may be the only efficient means of transfection in some cell lines, use of these cells will not be preferred if another means of transfection is desired.

Expression of the UTR-associated reporter gene will be compared to expression of the non-UTR associated second reporter gene. Any discrepancies in this ratio of expression could reflect UTR-mediated changes in mRNA translation, export, or stability. Many potential schemes for detecting expression, and identifying expression-altering UTRs are available. Particularly well-suited system those that produce a colored or otherwise detectable product as determined by gel electrophoresis, detection of fluorescence, chemiluminescence, or antibody binding. For example, cells that express such UTRs can be identified and isolated using a fluorescence activated cell sorter (FACS) and green fluorescent protein (GFP) as a reporter gene (Bierhuizen et al., Biochem. Biophys. Res. Commun. 234: 371–375, 1997; Grignani et al., Cancer Res. 58: 14–19, 1998; de Martin et al., Gene Ther. 4: 493–495, 1997; Foster et al., J. Virol. Methods 75: 151–60, 1998). Such a system is advantageous for high throughput screening. Other systems that can be used to track gene expression include detecting *E. coli* lacZ-encoded β-galactosidase activity coupled with a fluorogenic substrate (Flering et al., Cytometry 12: 291–301, 1991) and detecting the expression of foreign cell-surface antigens by means of fluorescently-labeled antibodies (Planelles et al., Gene Ther. 2: 369–76, 1995).

In the case of detection by fluorescence, the emission spectra of the fluorophores used to track expression of the UTR-associated first reporter genes and non-UTR associated second reporter genes must be sufficiently different so that, for example, the FACS instrument can perform two-color analysis and sort cells on the basis of the correlation between expression of the two reporter genes. The transfected cell population will consist of four different expression patterns as follows: 1) cells that are negative for both gene markers, indicating transfection failure; 2) cells with a ratiometric relationship between expression of the UTR-linked gene and the control gene, indicating that the UTR has no effect on gene expression; 3) cells with disproportionately higher expression of the UTR-linked gene, indicating that the UTR enhances translation efficiency or mRNA stability; and 4) cells with disproportionately lower UTR-linked gene expression, indicating that the UTR reduces translation efficiency or mRNA stability.

Following FACS sorting, cells with skewed fluorescence signals can be collected for further analysis. The sequence of the expression altering UTR can be determined using, for example, PCR with vector primers, or plasmid rescue. One fluorescent color readout is dependent upon levels of expression of UTR-linked second reporter gene and the other color is dependent upon the level of expression of the UTR-linked gene. The FACS instrument is capable of determining the levels of expression of both colors simultaneously and plots the two levels for each individual cell versus each other. It is expected that most UTRs will not affect gene expression and therefore, a majority of the transfected cells should express a consistently proportional level of both gene products. This population of cells will occupy a characteristic region of the two color plot. Cells that fall outside of this region will be automatically sorted into one of two tubes with UTR-linked genes that proportionally up-regulate gene expression in one tube and UTR-linked genes that down-regulate gene expression in the other.

A similar strategy can be used to screen and identify compounds that affect the function of the 5' and 3' UTR regulatory elements. Compounds that modulate the UTR effect on gene expression would skew the expression of the UTR-linked gene as compared to gene expression in the absence of the compound.

EXAMPLE 1

Selective RNase H Digestion of mRNA

Figure 1:
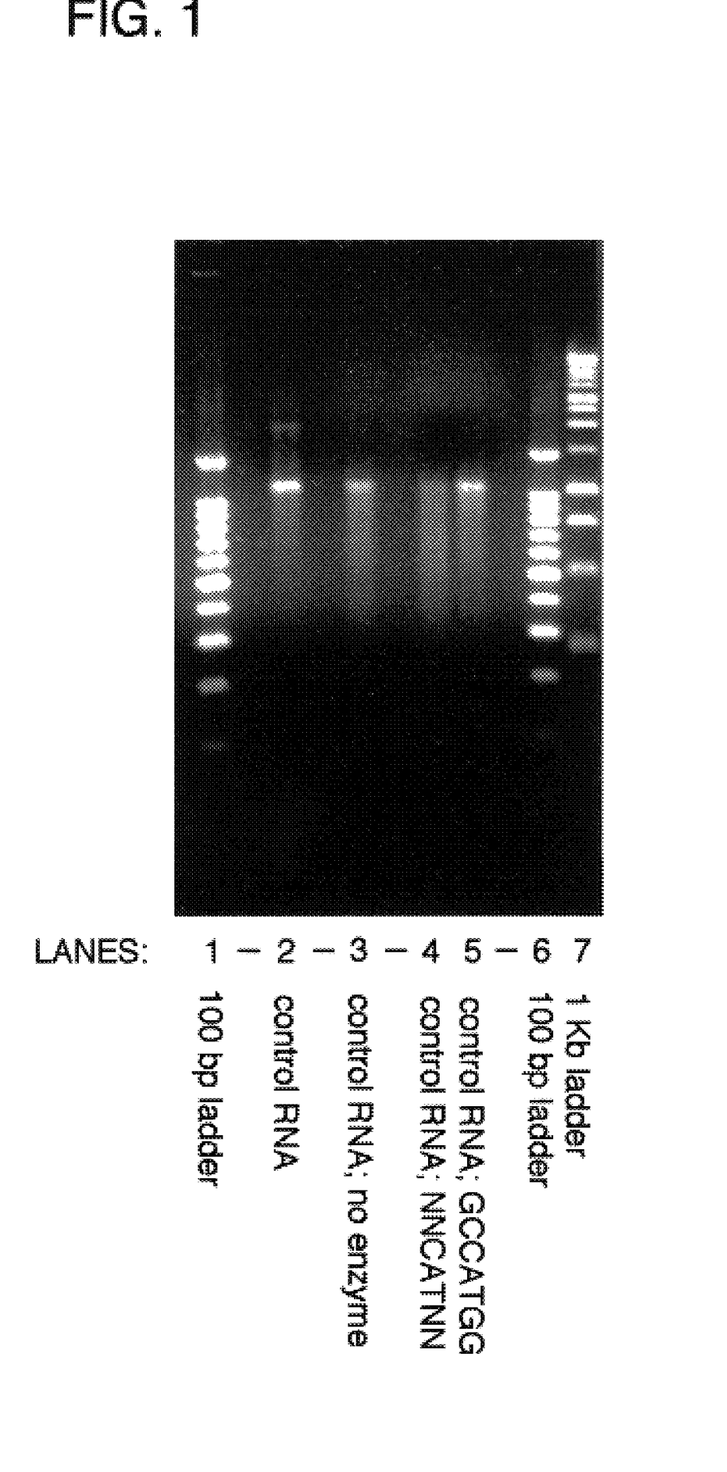
FIG. 1 demonstrates RNase H digestion of a control RNA sequence using specific or partially degenerate oligodeoxynucleotide 7-mers conditions that allow hydrolysis only if 6 or more consecutive base pairs are hybridized (compare lanes 4 and 5).

Conditions for digestion can be adopted that prevent RNase H hydrolysis unless mRNA hybridization to the oligodeoxynucleotide probe encompasses more than 5 or 6 consecutive nucleotides. This was demonstrated in an experiment in which a 7-mer oligodeoxynucleotide was designed to hybridize to a control mRNA species at multiple locations, but to form no more than five consecutive DNA/RNA base pairs at any one of these locations. No hydrolysis occurred using this oligodeoxynucleotide, but it did occur using a partially degenerate oligodeoxynucleotide, NNCATNN (where N is an equimolar mixture of A, C, G, and T) which allowed hybridization of 6 or 7 consecutive base pairs (see FIG. 1). Following denaturation of 0.2 μg control RNA (Promega luciferase control sequence) and 70 pmol oligodeoxynucleotide in 10 mM Tris HCl, pH 8.0, 50 mM NaCl, at 70° C. for 10 minutes, samples were submerged in ice. RNase H, $MgCl_2$, and DTT were added to final concentrations of 0.4 units, 5 mM , and 1 mM, respectively. Samples were incubated at 20° C. for 60 minutes. The reactions were terminated by the addition of EDTA to a final concentration of 25 mM, and digestion products were separated and visualized on a 1% TBE non-denaturing agarose gel stained with ethidium bromide.

Figure 2:
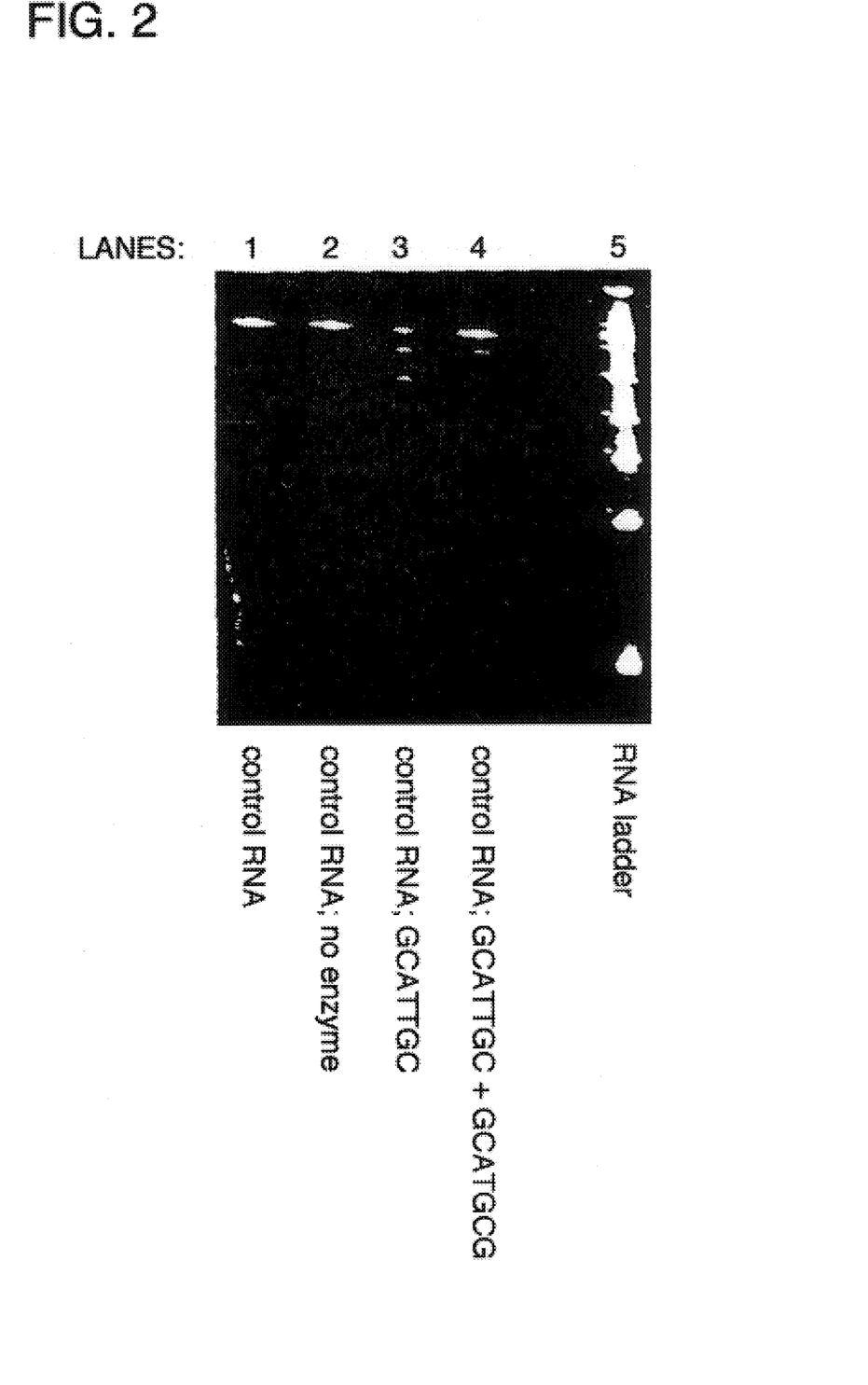
FIG. 2 demonstrates RNase H digestion of a control sequence using two different sequence specific oligodeoxynucleotides, under conditions that allow hydrolysis only if 7 consecutive base pairs are hybridized (see lane 3).

Conditions for RNase digestion can also be controlled such that a sequence-specific oligodeoxynucleotide 7-mer will mediate RNase H-catalyzed hydrolysis of RNA only at the single site where seven consecutive DNA/RNA base pairs can form (see FIG. 2). These conditions included denaturing 0.2 µg control RNA (Promega luciferase control sequence) and 250 nmol oligodeoxynucleotide in 10 mM Tris HCl, pH 8.0, 50 mM NaCl, at 70 C. for 10 minutes before submerging the samples in ice. Following the addition of RNase H, $MgCl_2$, and DTT, as described above, and incubation at 20° C. for 60 minutes, the digestion was terminated with the addition of EDTA to a final concentration of 25 mM. Digestion products were separated and visualized on a 6% polyacrylamide gel stained with ethidium bromide.

Figure 3:
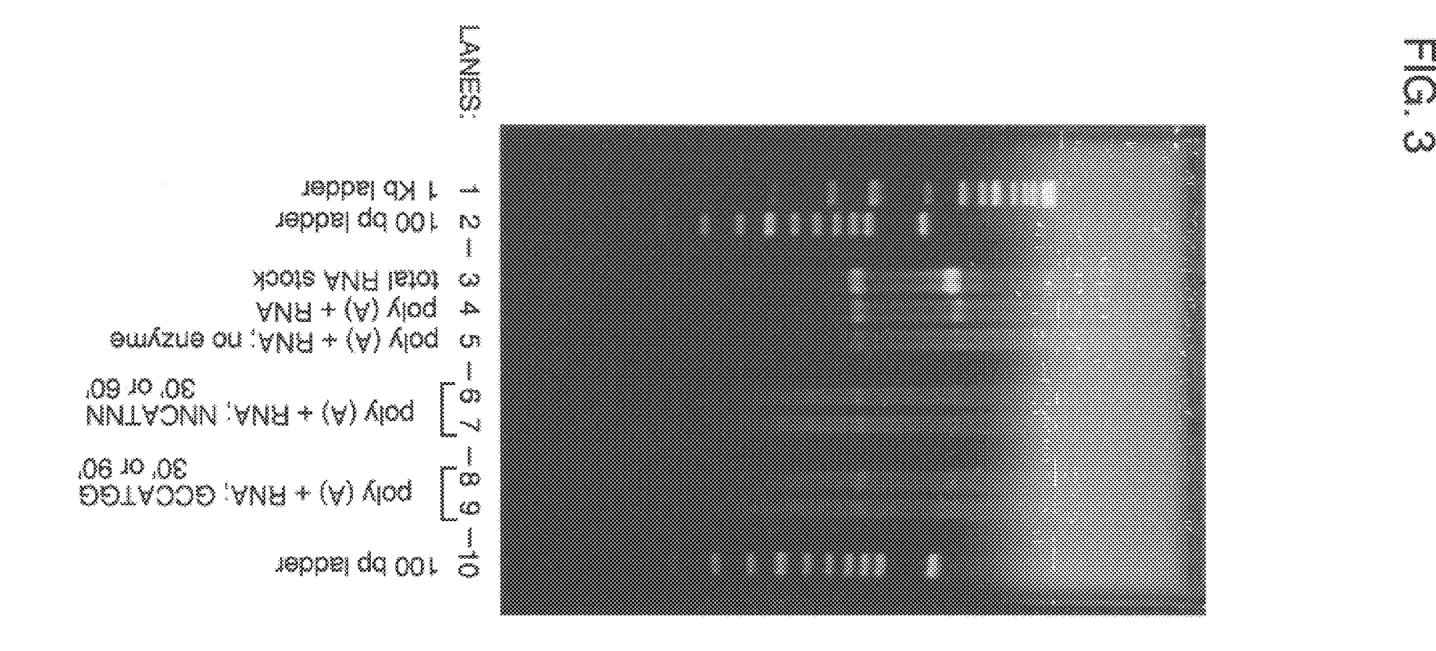
FIG. 3 shows RNase H digestion of poly(A)+ RNA using a partially degenerate oligonucleotide 7-mer, under conditions that allow hydrolysis only if 7 consecutive base pairs are hybridized. The number of hydrolysis sit s can be limited, even after extended incubation (compare lanes 6 and 7).

A population of poly(A)+ RNA can be substituted for a control mRNA, and the poly(A)+ RNA can be partially hydrolyzed with a degenerate oligodeoxynucleotide, as shown in FIG. 3. Thus; under conditions that prevent formation of fewer than seven consecutive DNA/RNA base pairs for hydrolysis by RNase H, a partially degenerate oligodeoxynucleotide can be used in the reaction with poly(A)+ RNA, and the number of hydrolysis sites can still be limited, even after an extended incubation period.

EXAMPLE 2
Use of Ribosomes to Construct Full Length 3' UTRs

Figure 4:
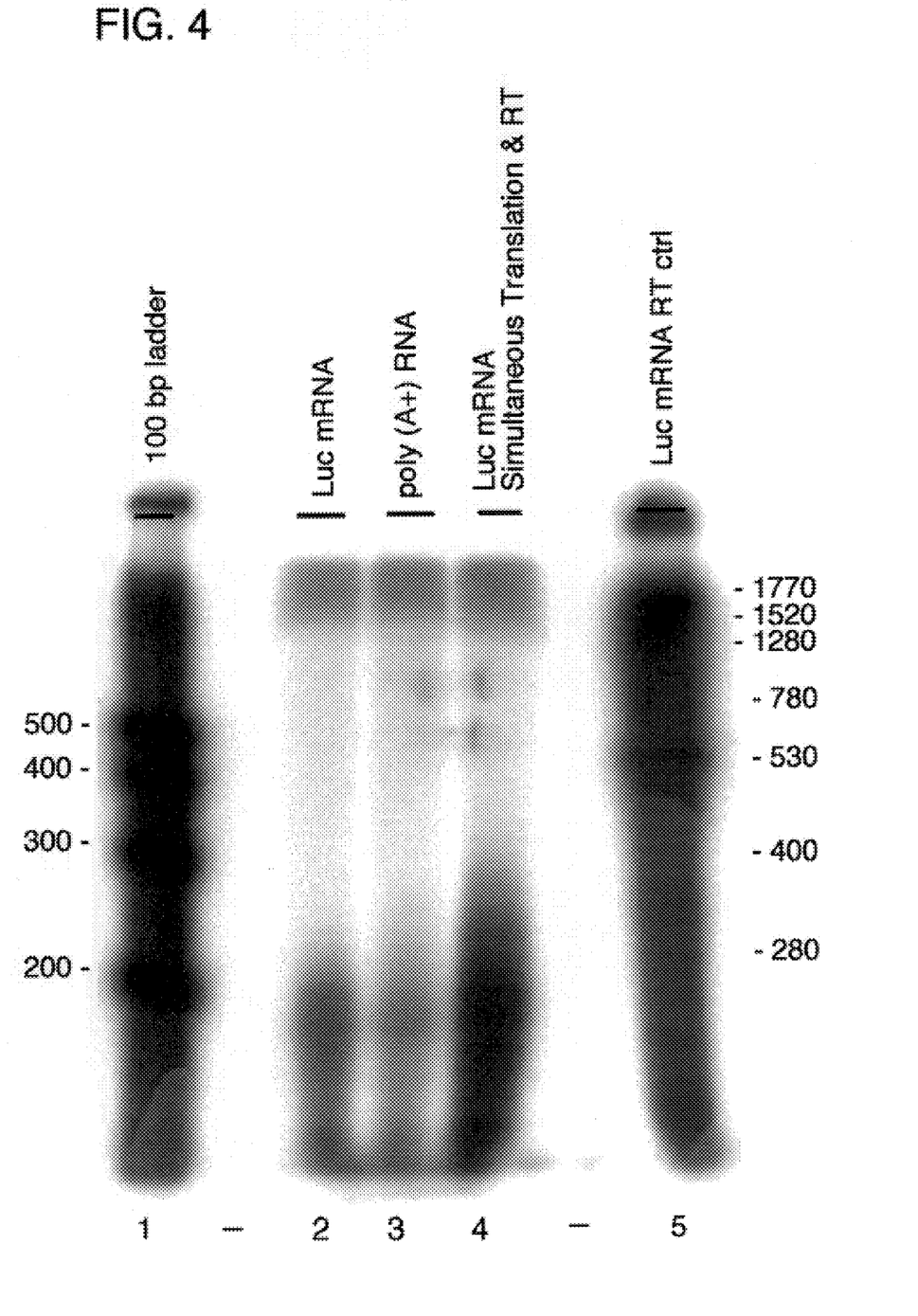
FIG. 4 illustrates limited reverse transcription of 3' UTR sequences.

Using reverse transcription and an oligo(dT) primer, a full length 3' UTR sequence can be copied to cDNA. Reverse transcription begins with the poly(A) region and proceeds upstream towards the 5' end of the 3' UTR. To terminate transcription at the coding sequence termination site, the mRNA is fully loaded with actively translating ribosomes which cause steric hindrance of the transcriptase. Given that ribosomes do not bind mRNA downstream of the termination codon, the reverse transcriptase proceeds unhindered to copy the entire 3' UTR sequence, but the activity of the reverse transcriptase is then terminated, effectively separating the full length 3' UTR from any upstream coding sequence (see FIG. 4).

Other Embodiments

All publications mentioned herein are hereby incorporated by reference.

What is claimed is:

1. A cDNA library comprising at least 100 different cDNA molecules, said cDNA molecules comprising sequences that correspond to at least 100 different mRNA untranslated regions (UTRs) of unknown sequence, said UTRs being isolated and separate from adjacent mRNA coding regions.

2. A cDNA library, wherein said library is constructed by steps comprising
   a) purifying poly(A)+ RNA from total RNA;
   b) performing controlled, non-random enzymatic digestion of AUG sequences in the poly (A)+ RNA;
   c) purifying said digested RNA to obtain the fragments containing the 5' end sequences; and
   d) synthesizing cDNA from the purified RNA obtained in step (c);
      wherein said library comprises cDNA molecules, said cDNA molecules comprising sequences that correspond to different mRNA 5' UTRs, and said UTRs being isolated and separate from adjacent mRNA coding regions.

3. The cDNA library of claim 2, wherein said enzymatic digestion is carried out using RNase H.

4. A cDNA library, wherein said library is constructed by steps comprising
   a) purifying poly(A)+ RNA from total RNA;
   b) synthesizing nucleic acid heteroduplexes from said poly(A)+ RNA using degenerate primers that hybridize to the region surrounding and including the initiation codon, said heteroduplexes comprising the 5' end sequences of said RNA;
   c) purifying the heteroduplexes obtained in step (b) to obtain the fragments containing the 5' end sequences; and
   d) synthesizing cDNA from the purified heteroduplexes obtained in step (c);
      wherein said library comprises cDNA molecules, said cDNA molecules comprising sequences that correspond to mRNA 5' UTRs, and said UTRs being isolated and separate from adjacent mRNA coding regions.

5. The cDNA library of claim 2 or 4, wherein said 5' sequence purification is carried out using a cap binding protein.

6. The cDNA library of claim 1, 2, or 4, wherein said cDNA molecules are cloned into a vector system that can express said molecules.

SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: Based on vertebrate mRNA
<221> NAME/KEY: variation
<222> LOCATION: (4)...(4)
<223> OTHER INFORMATION: n = g or a.

<400> SEQUENCE: 1 gccnccaugg                                                          10

7. A cDNA library, where said library is constructed by the steps comprising
   a) purifying poly(A)+ RNA from total RNA;
   b) performing random digestion on the poly(A)+ RNA;
   c) purifying said digested RNA to obtain poly(A) containing fragments; and
   d) synthesizing cDNA from the purified RNA obtained in step (c);
      wherein said library comprises cDNA molecules, said cDNA molecules comprising sequences that correspond to at least 100) different 3' UTRs of unknown sequence, and said UTRs being isolated and separate from adjacent mRNA coding regions.

8. A cDNA library, wherein said library is constructed by the steps comprising
   a) purifying poly(A)+ RNA from total RNA
   b) loading said poly(A)+ RNA with ribosomes; and
   c) performing reverse transcription on said loaded poly (A)+ RNA using an oligo(dT) primer and polymerase;
      wherein said library comprises cDNA molecules, said cDNA molecules comprising sequences that correspond to at least 100 different 3' UTRs of unknown sequence, and said UTRs being isolated and separate from adjacent mRNA coding regions.

9. The cDNA library of claim 7 or 8, wherein said cDNA molecules are cloned into a vector system that can express said molecules.

10. The cDNA library of claim 1, 2, 4, 7, or 8, wherein said library comprises isolated full-length UTRs.

11. A vector comprising
   a) a nucleotide sequence encoding an mRNA UTR in operative linkage to a promoter, wherein said nucleotide sequence is derived from a cDNA library of cDNA molecules comprising sequences that correspond to different UTRs, said UTRS being isolated and separate from adjacent mRNA coding regions:
   b) a first reporter gene positioned for transcription upstream or downstream of said UTR-encoding nucleotide molecule; and
   c) a second, different reporter gene in operative linkage to a promoter but unassociated with said UTR-encoding nucleotide molecule.

12. The vector of claim 11, wherein said reporter genes encode a fluorescent protein or cell surface marker protein.

13. A method of identifying a regulatory UTR, said method comprising
   a) transfecting a plurality of host cells with a plurality of vectors of claim 11, wherein said host cells are transfected with different UTR-encoding molecules;
   b) sorting cells on the basis of the ratio between expression of the first reporter gene and the second reporter gene;
   c) identifying the cells of step (a) that have skewed expression ratios as compared to the population of cells of step (a) as a whole, or as compared to cells transfected with a vector that encodes the first and second reporter gene, but lacks the corresponding UTR-encoding molecule; and
   d) sequencing the UTR expressed in said identified cells.

14. The method of claim 13, wherein said gene expression is detected by emission of fluorescence.

15. The method of claim 14, wherein said cells are sorted by a fluorescence activated cell sorter.

16. A cell transfected with the vector of claim 11.

17. A method of constructing a cDNA library, said method comprising:
   a) purifying poly(A)+ RNA from total RNA;
   b) performing controlled, non-random enzymatic digestion of AUG sequences in the poly (A)+ RNA;
   c) purifying said digested RNA to obtain the fragments containing the 5' end sequences; and
   d) synthesizing cDNA from the purified RNA obtained in step (c);
      wherein said library comprises cDNA molecules, said cDNA molecules comprising sequences that correspond to different mRNA 5' UTRs, and said UTRs being isolated and separate from adjacent mRNA coding regions.

18. The method of claim 17, wherein said enzymatic digestion is carried out using RNase H.

19. A method of constructing a cDNA library, said method comprising:
   a) purifying poly(A)+ RNA from total RNA;
   b) synthesizing nucleic acid heteroduplexes from said poly(A)+ RNA using degenerate primers that hybridize to the region surrounding and including the initiation codon, said heteroduplexes comprising the 5' end sequences of said RNA;
   c) purifying the heteroduplexes obtained in step (b) to obtain the fragments containing the 5' end sequences; and
   d) synthesizing cDNA from the purified heteroduplexes obtained in step (c);
      wherein said library comprises cDNA molecules, said cDNA molecules comprising different mRNA 5' UTRs, said UTRs being isolated and separate from adjacent mRNA coding regions.

20. The method of claim 17 or 19, wherein said 5' sequence purification is carried out using a cap binding protein.

21. The method of claim 17 or 19, wherein said cDNA molecules are cloned into a vector system that can express said molecules.

22. A method of constructing a cDNA library, said method comprising:
   a) purifying poly(A)+ RNA from total RNA;
   b) performing random digestion on the poly(y)+ RNA;
   c) purifying said digested RNA to obtain poly(A) containing fragments; and
   d) synthesizing cDNA from the purified RNA obtained in step (c);
      wherein said library comprises cDNA molecules, said cDNA molecules comprising sequences that correspond to different 3' UTRs, said UTRs being isolated and separate from adjacent mRNA coding regions.

23. A method of constructing a cDNA library, wherein said method comprises
   a) purifying poly(A)+ RNA from total RNA;
   b) loading said poly(A)+ RNA with ribosomes; and
   c) performing reverse transcription on said loaded poly (A)+ RNA using an oligo(dT) primer and polymerase;
      wherein said library comprises cDNA molecules, said cDNA molecules comprising sequences that correspond to different 3' UTRs, and said UTRs being isolated and separate from adjacent mRNA coding regions.

24. The method of claim 22 or 23, wherein said cDNA molecules are cloned into a vector system that can express said molecules.

25. The method of claim 17, 19, 22, or 23, wherein said cDNA molecules have sequences that correspond to at least 100 different UTRs.

26. The cDNA library of claim 2 of 4, wherein said cDNA molecules comprising sequences that correspond to at least 100 different UTRs.

27. The cDNA library of claim 2 or 4, wherein said library is constructed from total cellular RNA.

28. The method of claim 13, further comprising contacting said host cells with a candidate compound.

29. The vector of claim 11, wherein sad cDNA library is the cDNA library of claims 1, 2, 4, 7, or 8.

30. The cDNA library of claim 2 or 4, wherein said cDNA molecules comprise sequences that correspond to at least 100 different mRNA untranslated regions (UTRs) of unknown sequence.

31. The method of claim 13, 17, 19, 22, or 23, wherein said cDNA molecules comprise sequences that correspond to at least 100 different mRNA untranslated regions (UTRs) of unknown sequence.

32. The cDNA library of claims 1, 2, 4, 7, or 8, wherein said cDNA molecules comprise sequences that correspond to at least 100 different uncharacterized UTRs.

33. The method of claim 13, 17, 19, 22, or 23, wherein said cDNA molecules comprise sequences that correspond to at least 100 different uncharacterized UTRs.

* * * * *